United States Patent
Knifton et al.

(10) Patent No.: US 6,315,964 B1
(45) Date of Patent: Nov. 13, 2001

(54) PROCESS AND SYSTEM FOR ALKYLATION OF AROMATIC COMPOUNDS

(75) Inventors: John F. Knifton; Prakasa Rao Anantaneni, both of Austin; Melvin Stockton, Georgetown, all of TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 08/879,745

(22) Filed: Jun. 20, 1997

Related U.S. Application Data

(62) Division of application No. 08/598,695, filed on Feb. 8, 1996, now Pat. No. 5,770,782.

(51) Int. Cl.⁷ ................................. B01J 8/02; B01J 10/00
(52) U.S. Cl. ......................... 422/190; 422/188; 422/234
(58) Field of Search ...................... 422/187, 188, 422/189, 190, 191, 193, 194, 198, 106, 211, 234, 235

(56) References Cited

U.S. PATENT DOCUMENTS

| | | | |
|---|---|---|---|
| 4,301,316 | * 11/1981 | Young | 585/455 |
| 4,301,317 | 11/1981 | Young | 585/455 |
| 4,973,780 | 11/1990 | Johnson et al. | 585/467 |
| 5,034,564 | 7/1991 | Kocal | 585/467 |
| 5,086,193 | 2/1992 | Sy | 585/446 |
| 5,146,026 | 9/1992 | Tejero et al. | 585/467 |
| 5,171,896 | * 12/1992 | Knifton et al. | 568/791 |
| 5,171,904 | 12/1992 | Sanderson et al. | 585/10 |
| 5,196,574 | 3/1993 | Kocal | 562/94 |
| 5,273,644 | 12/1993 | Wegerer | 208/66 |
| 5,344,997 | 9/1994 | Kocal | 568/628 |
| 5,362,377 | * 11/1994 | Marker | 208/133 |
| 5,446,223 | 8/1995 | Smith, Jr. | 585/313 |
| 5,498,317 | * 3/1996 | Holiday | 202/154 |

FOREIGN PATENT DOCUMENTS

| | | |
|---|---|---|
| 0 160 144 | 11/1985 | (EP) . |
| 0 160 145 | 11/1985 | (EP) . |
| 0 353 813 | 2/1990 | (EP) . |

OTHER PUBLICATIONS

Almeida, J. L. G. de, M. Dufaux, Y. B. Taarit and C. Naccache, Effect of pore size and aluminium content on the production of linear alkylbenzenes over HY, H–ZSM–5 and H–ZSM–12 zeolites: alkylation of benzene with 1–dodecene, *Applied Catalysis A: General*114: 141–159, 1994.

Almeida, J. L. G. de, M. Dufaux, Y. B. Taarit and C. Naccache, Linear alkylbenzene, JAOCS 71 (7): 675–694, 1994.

Cohen, L., R. Vergara, A. Moreno and J. L. Berna, Influence of 2–phenyl alkane and tetralin content on solubility and viscosity of linear alkylbenzene sulfonate, JAOCS 72 (1): 115–122, 1995.

Venuto, P. B., L. A. Hamilton, P. S. Landis and J. J. Wise, Organic reactions catalyzed by crystalline aluminosilicates I. alkylation reactions, *Journal of catalysis* 4: 81–98, 1966.

\* cited by examiner

*Primary Examiner*—Marian C. Knode
*Assistant Examiner*—Alexa A. Doroshenk
(74) *Attorney, Agent, or Firm*—O'Keefe, Egan & Peterman LLP

(57) ABSTRACT

This invention is directed to a reactive distillation process and system for the alkylation of liquid aromatic compounds with a liquid olefin or olefin/paraffin mixture. The aromatic compound may have from about 6 to about 30 carbons and the olefin may have from about 8 to 30 carbons. The system has a reactor configuration utilizing an alkylation catalyst, a reboiler with product takeoff, and a feed inlet above the catalyst bed. The system may also include a means for in-situ mixing of the aromatic compound and olefin or olefin/paraffin mixture, an overhead condenser and/or a water takeoff.

8 Claims, 2 Drawing Sheets

PROCESS AND SYSTEM FOR ALKYLATION OF AROMATIC COMPOUNDS

This application is a division of application Ser. No. 08/598,695, filed Feb. 8, 1996, now U.S. Pat. No. 5,770,782.

BACKGROUND OF THE INVENTION

This invention generally relates to a reactive distillation process and system for the alkylation of aromatic compounds with olefins.

Alkylated aromatics, including linear alkyl benzenes (LAB's) having long chains (typically 10–14 carbons), are commonly used, commercial products. LAB's are commonly sulfonated to thereby produce surfactants.

Typically, alkylated aromatics are manufactured commercially using classic Friedal-Crafts chemistry, employing catalysts such as aluminum chloride, or using strong acid catalysts such as hydrogen fluoride, for example, to alkylate benzene with olefins. While such methods produce high conversions, the selectivity to the 2-phenyl isomer is low, generally being about 30% or less. LAB's with a high percentage of the 2-phenyl isomer are highly desired because such compounds when sulfonated have long "tails" which provide enhanced solubility and detergent properties.

Reactive distillation methods for producing short chain alkylated aromatics are known. These methods are typically directed toward reacting gaseous phase short chain olefins, such as ethylene or propylene, with benzene.

SUMMARY OF THE INVENTION

It has now been recognized that alkylation reactions using long chain olefins present peculiar problems. With longer chain liquid olefin reactants, lower space velocities may be necessary due to the low mutual solubilities of the feed components. Due to lower reaction temperatures, alkylation reactions involving long chain olefins may be prone to the accumulation of water brought into the alkylation unit with the feeds or formed as a by-product in the catalyst bed, leading to deactivation of the catalyst. Furthermore, because liquid olefins mix much less readily with liquid aromatics than do gaseous olefins, different mixing procedures are necessary in order to achieve high yields of desired LAB's. In addition, the use of longer chain liquid olefin reactants may lead to a greater tendency for the formation of carbonaceous deposits and heavy organics on the catalyst bed. The formation of carbonaceous deposits and heavy organics on the catalyst bed. By-product formation may generally be more difficult to control with the higher molecular weight olefin coreactants.

Therefore, a need exists for a method of alkylation of aromatics with long chain olefins that has high olefin conversion, high selectivity and having long catalyst lifetimes. In particular, a need exists for a method of producing alkylated aromatics from liquid industrial reactant feeds containing water that avoids water deactivation of the catalyst and which ensures adequate mixing of the liquid aromatic and olefin reactants. A need also exists for such a method having high substrate olefin conversion and long catalyst lifetimes. More particularly, a need exists for a method of LAB production having high substrate olefin conversion, high selectivity to 2-phenyl isomer LAB, and employing a catalyst having long lifetimes and easy handling. LAB is useful as starting material to produce sulfonated LAB, which itself is useful as a surfactant. This invention provides a solution to one or more of the problems and disadvantages described above.

This invention, in one broad respect, is a process useful for preparing alkylated aromatic compounds comprising introducing an aromatic compound having from about 6 to about 30 carbons and an olefin having from about 8 to about 30 carbons above a catalyst bed containing an alkylation catalyst under conditions such that the olefin and the aromatic compound react to form an alkylated aromatic compound; allowing the alkylated aromatic compound and unreacted aromatic compound to descend into a reboiler from the catalyst bed; withdrawing the alkylated aromatic compound from the reboiler; and heating contents of the reboiler such that the aromatic compound refluxes to contact the catalyst bed.

In a second broad respect, this invention is a system for manufacturing alkylated aromatic compounds, comprising a reactor containing an alkylation catalyst bed; one or more injectors in the reactor for introducing aromatic compound, olefin or a mixture of aromatic compound and olefin above the catalyst bed; a reboiler for collecting, heating and refluxing unreacted aromatic compound descending from the reactor, the reboiler positioned below and in communication with the reactor, the reactor and reboiler being generally in vertical alignment; and a means for withdrawing alkylated aromatic compound from the reboiler.

Use of the process and system of this invention for alkylation of aromatics with long chain olefins, particularly α-olefins, or long chain olefin/paraffin mixed feed stocks advantageously achieves high conversion rates and long catalyst lifetimes by using the reactor configuration specified above. When the process and system of this invention is used for selective benzene monoalkylation by liquid olefin or liquid olefin/paraffin mixed feed stocks, high selectivity to 2-phenyl product isomers is advantageously obtained. Additional benefits may be derived from the process and system of this invention by utilizing a column of solid acid catalyst and a water condenser with water take-off above the catalyst bed as depicted, for instance, in FIG. 1 and FIG. 2. A process operated in accordance with the representative apparatus of this invention depicted in FIG. 1 and FIG. 2 has the advantage that rising benzene vapor from the reboiler continuously cleans the catalyst of heavy organics to thereby increase lifetime of the catalyst. Improved catalyst life and performance during benzene alkylation is enhanced by continuous water removal from the catalyst bed (without the need for a predrying step) and by better mixing of the reactants and increased effective benzene concentration in the alkylation reaction zone. In addition, when used for selective benzene monoalkylation this invention advantageously produces only low amounts of dialkylated benzene, which is not particularly as useful for detergent manufacture, as well as only low amounts of tetralin derivatives.

Certain terms and phrases have the following meanings as used herein.

"Meq/g" means milliequivalents of titratable acid per gram of catalyst, which is a unit used to describe acidity of the catalysts. Acidity is generally determined by titration with a base, as by adding excessive base, such as sodium hydroxide, to the catalyst and then back titrating the catalyst.

"Conv." and "Conversion" mean the mole percentage of a given reactant converted to product. Generally, olefin conversion is about 95 percent or more in the practice of this invention.

"Sel." and "Selectivity" mean the mole percentage of a particular component in the product. Generally, selectivity to the 2-phenyl isomer is about 70 or more in the practice of this invention.

DETAILED DESCRIPTION OF THE PREFERRED EMBODIMENTS

Catalysts

Figure 1:
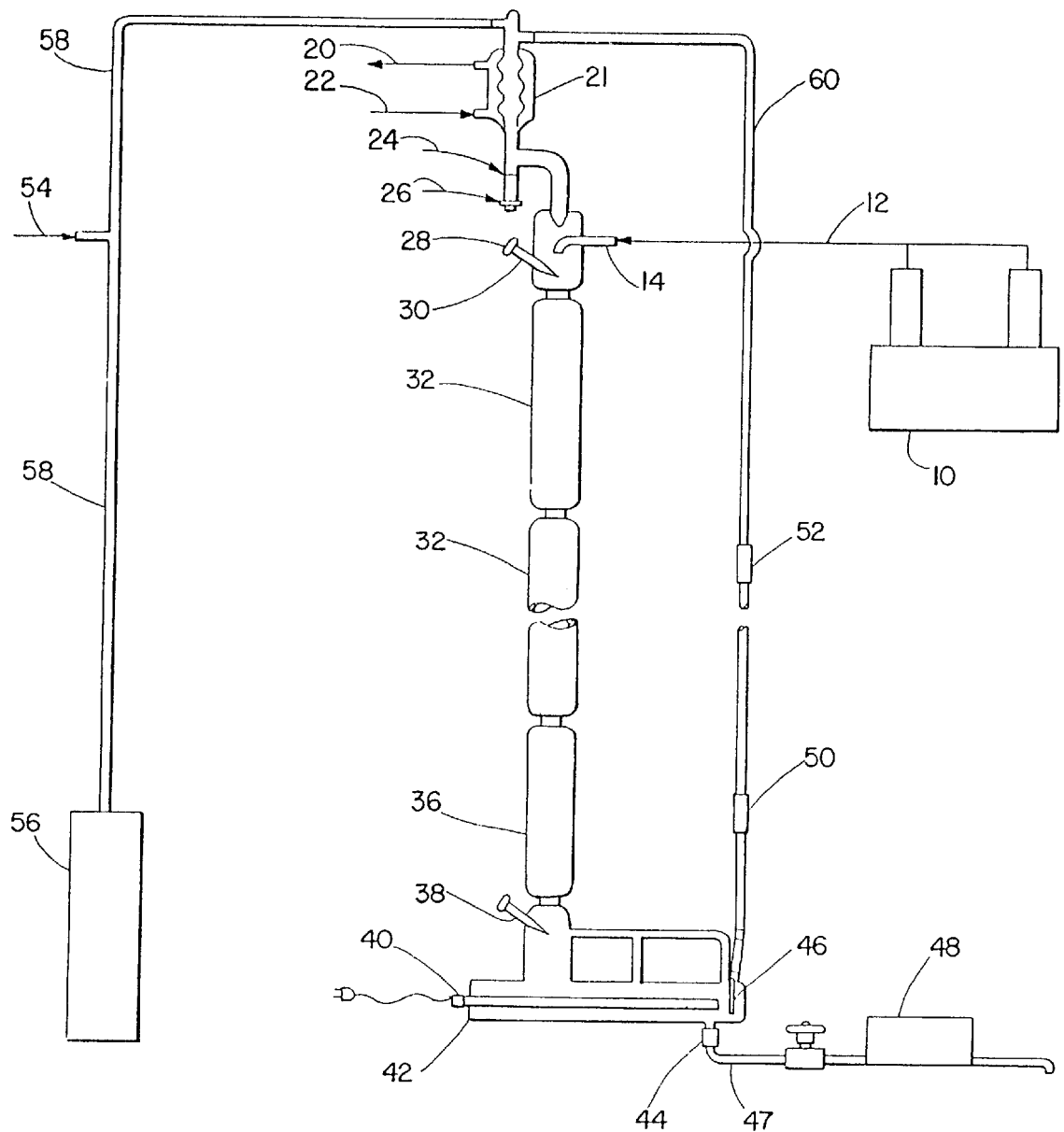
FIG. 1 shows a representation of a first continuous reactive distillation column employed in the practice of this invention.

Catalysts that may be employed in the practice of this invention include any solid acid alkylation catalyst. Representative examples of such solid catalysts include acidic zeolitic materials such as acidic y-zeolites, β-zeolites, acidic mordenites, acidic clays (particularly acidic montmorillonite clays), fluorided montmorillonite clays, fluorided β-zeolites, fluorided mordenites and silica-alumina combinations among others. Other catalysts that may be employed in the practice of this invention include those comprising a heteropoly acid, mineral acid, or phosphoric acid in combination with zeolite or non-zeolite solid inorganic oxide supports, large pore crystalline molecular sieve and/or ion exchange resin, as well as mineral acid and carboxylic acid treated zeolites, such as mordenites.

Acidic zeolites that may be employed in the process and system of this invention include both naturally occurring and synthetic silica-alumina zeolites. Acceptable acidic zeolites are characterized as being preferably dealuminized or as having a reduced alkali metal content and include those based on A, X, Y, and L type zeolites, erionite, omega, beta, and mordenite. Other acceptable acidic molecular sieve catalysts include any of the various types of mole sieves having reduced alkali metal content. Preferred acidic zeolites for this invention are β-zeolite and dealuminated mordenite.

The non-zeolitic solid inorganic oxide that may be employed with a Bronsted or Lewis acid in the process and system of this invention may be selected from among the inorganic oxides including alumina, silica, boria, titanium dioxide, zirconium dioxide, chromia, zinc oxide, magnesia, calcium oxide, silica-alumina. silica-magnesia, silica-alumina-magnesia, silica-alumina-zirconia. chromia-alumina, alumina-boria, silica-zirconia, etc. and the various naturally occurring inorganic oxides of various states of purity such as bauxite, clay, diatomaceous earth, etc. The preferred inorganic oxide is a solid acid montmorillonite catalyst, particularly an acidic fluorided montmorillonite clay.

The large and medium pore crystalline zeolites that may be employed with a Bronsted or Lewis acid in the process and system or this invention include zeolites such as ZSM-5, ZSM-12, ZSM-18, ZSM-20, zeolite Beta, zeolite L, mordenite, faujasite, zeolite Y, zeolite X and the rare earth metal-containing forms of the above.

Other large pore ordered structures which can be used with a Bronsted or Lewis acid in the present invention include pillared silicates and/or clays; aluminophosphates, e.g. ALPO-5, VPI-5; silicoaluminophosphates, e.g. SAPO-5, SAPO-37, SAPO-31, SAPO-40, SAPO-41; as well as other metal aluminophosphates.

The ion exchange resins that may be employed in the process and system of the present invention include those macroreticular acid ion exchange resins having sulfonic acid groups, e.g., the sulfonated styrene-divinylbenzene copolymer exchange resins such as those commercially available as Amberlyst-15, Amberlyst XN-1005, Amberlyst XN-1010, Amberlyst XN-1011, Amberlyst XN-1008 and Amberlite 200. Microreticular acid ion exchange resins, such as Amberlite IR-120H may also be acceptable in the practice of this invention.

Catalyst Preparation

One preferred catalyst of this invention is a fluorine-containing mordenite. Mordenite is a type of zeolite. This catalyst is prepared from acidic mordenite (typically having 0.1 percent or less of sodium) having a silica-alumina molar ratio of from about 10:1 to about 100:1. More typically, the starting mordenite has a silica/alumina molar ratio of from about 10:1 to about 50:1. The starting hydrogen mordenite, which is commonly available commercially, is treated with an aqueous solution of hydrogen fluoride ("HF") to produce the active, long-life and highly selective catalyst of the invention. In the course of such HF treatment, as well as during subsequent calcination of said HF-treated mordenite, the silica/alumina molar ratio typically increases. The finished catalysts of this invention show a fluorine content of from about 0.1 to about 4 percent by weight, more typically about 1 percent.

While not wishing to be bound by theory, it is believed that the HF reacts with sites where —Si—O—Al— linkages occur such that the linkage is broken with fluorine becoming bonded to the Al such that —Si—OH and F—Al— groups form. This is believed to decrease the total Bronsted acid sites and increase the strength of the remaining acid sites in the mordenite and is believed to stabilize the acidity of the mordenite such that the mechanisms which degrade performance during LAB production, such as coke build-up, are retarded.

The aqueous solution used to treat the mordenite may contain a range of HF concentrations. Generally, the HF concentration is a minimum of about 0.1 percent by weight. Below such minimum concentration, the effect of the fluorine treatment significantly decreases, resulting in the undesirable need for repeated treatments. Generally, the HF concentration on the upper end is about 10 percent by weight or less. Above a concentration of about 10 percent by weight, the HF is so concentrated that it is difficult to prevent HF from destroying the crystallinity of the mordenite, thereby detrimentally affecting its efficacy as a catalyst for LAB production.

The aqueous HF solution may be prepared by diluting commercially available 48% HF solutions to the desired concentration. Alternatively, HF can be sparged into water to provide an aqueous HF solution.

Typically, the treatment is carried out by adding mordenite powder or pellets to a stirred aqueous HF solution at a temperature of from about 0° C. to about 50° C. The stirring and contacting is continued for a time sufficient to achieve the desired level of fluorine in the mordenite. This time may vary depending on factors such as HF concentration. amount of HF solution relative to the amount of mordenite being treated, stirring speed or speed of whatever agitation is employed, and temperature. After treatment, the mordenite can be recovered as by filtration, and then dried. It is also possible to impregnate the mordenite to incipient wetness with a given HF solution, as well as to treat the mordenite with gaseous hydrogen fluoride. Preferably said fluoride-treated mordenite would be calcined in air prior to use in alkylation service. The preferred calcination temperature would be in the range from about 400° C. to about 600° C. Alternative mordenite fluorinating agents to hydrofluoric acid and hydrogen fluoride include ammonium fluoride, fluorided silicon compounds and fluorided hydrocarbons.

The HF-treated mordenite of this invention generally has about 0.1 percent by weight or more of fluorine based on the total weight of the mordenite. Typically, the fluorine-containing mordenite contains about 4 percent by weight or less fluorine. The fluorine-containing mordenite most typically contains about 1 percent by weight of fluorine.

The mordenite can be used in the practice of this invention as a powder, in pellet form, as granules, or as extrudates. The mordenite can be formed into pellets or extrudates using binders well known to those of skill in the art, such as alumina, silica or mixtures thereof.

When used with this invention, fluorine treated mordenite catalyst advantageously produces high selectivities to the 2-phenyl isomer in the preparation of LAB, generally producing selectivities of about 70 percent or more. Also, when used in the apparatus of this invention, the fluorine treated mordenite enjoys a long lifetime, preferably experiencing only a 25 percent or less decrease in activity after 400 hours on stream.

Reactants for Production of Alklated Aromatics

In the practice of this invention, aromatic compounds are alkylated with olefins. These reactants can be handled and purified as is generally performed by those of skill in the art. In this regard, it is preferred that the reactants are water and alcohol free. The aromatics, which may contain one or more alkyl substituents, employed in the practice of this invention have a total number of carbons ranging from about 6 to about 30 carbons, preferably from about 6 to about 9 carbons. Representative examples of such aromatic reactants include benzene, toluene, cumene, decyl benzene, biphenyl, naphthalene, propyl benzene, xylene, ethyl toluene, diphenylmethane. styrene, diphenylethane, phenol, and benzyl halides. The olefins employed in the practice of this invention have from about 8 to about 30 carbons, preferably from about 10 to about 14 carbons, such as is available commercially or produced as dehydrogenated paraffin feed stocks. It is preferred that the olefin be monounsaturated. It is most preferred that the olefin be an alpha-olefin containing a terminal ethylenic unit.

Commonly, said olefins would be available in a paraffinic media of the same carbon range. Olefins in the 10 to 14 carbon number range would typically be available from $C_{10}$ to $C_{14}$ paraffin dehydrogenation in a $C_{10}$ to $C_{14}$ paraffin mixture having an olefin content of 5 to 20%. Often, the olefin content of said olefin-paraffin mixture would be 8 to 10 weight %.

An example of a compound produced using the process and system of the present invention for benzene monoalkylation is the 2-phenyl isomer of the LAB having the formula:

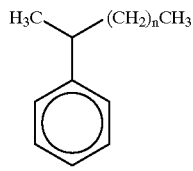

wherein n is from about 5 to about 17 and preferably from about 7 to about 11.

Process Conditions, Procedures, and Apparatus

In a preferred embodiment, the process of this invention can be carried out to monoalkylate benzene using the continuous reactive distillation column depicted in FIG. 1. In FIG. 1, a feed mixture of benzene and olefin, generally at a benzene-to-olefin molar ratio range of about 1:1 to 100:1 flows from feed pump 10 to feed inlet 14 via line 12. The feed mixture falls to packed mordenite catalyst bed 32 where alkylation in the presence of the fluorine-containing mordenite occurs. Alternatively, while not depicted in FIG. 1, the benzene and olefin can be introduced separately into the bed with mixing occurring in the bed, or the reactants can be mixed via an in-line mixer prior to introducing the reactants into the catalyst bed, or the reactants can be injected separately above the bed with mixing affected by use of standard packing above the bed, or the reactants can be sparged into the chamber above the bed. Because of the lack of affinity between liquid aromatics and olefins, mixing of the liquid reactants is important to achieve good conversion. Therefore, to achieve good conversion when the reactants are injected separately it is especially important to provide for mixing within the reactor.

The catalyst bed 32 depicted in FIG. 1 for laboratory scale may be made of two lengths of 1.1 inch internal diameter tubing, the lengths being 9.5 inches and 22 inches. In the catalyst bed 32, the falling feed mixture also contacts rising vapors of unreacted benzene which has been heated to reflux in reboiler 42 by heater 40. Such rising vapors pass over thermocouple 38 which monitors temperature to provide feedback to heater 40. The rising vapors of benzene and/or olefin also pass through standard packing 36 (e.g., 7.5 inches of goodloe packing). The rising vapors heat thermocouple 30 which connects to bottoms temperature controller 28 which activates heater 40 when temperature drops below a set level. Acceptable catalyst distillation structures for use in the process and system of the present invention include stars, doughnuts and spheres. Preferred catalyst distillation structures are extrudates, tablets, and granules.

Prior to startup, the system may be flushed with nitrogen which enters via line 54 and which flows through line 58. After startup, a nitrogen blanket is maintained over the system. Also prior to startup and during nitrogen flush, it may be desirable to heat catalyst bed 32 so as to drive off water from the fluorine-containing mordenite.

Residual water from the feed mixture or which otherwise enters the system is collected in water trap 24 upon being liquified at condenser 21 (along with benzene vapor). If the feed is very dry (free of water) the water trap 24 may not be needed. Removing water leads to longer catalyst lifetime. Hence, the water trap 24 is optional. The same applies to FIG. 2. Condenser 21 is cooled via coolant such as water entering condenser 21 via port 22 and exiting via port 20. As needed, water in water trap 24 may be drained by opening drain valve 26.

As needed, when LAB content in reboiler 42 rises to a desired level, the bottoms LAB product may be removed from the system via line 47, using either gravity or bottoms pump 48 to withdraw the product. When product is so withdrawn, valve 44 is opened.

In FIG. 1, dip tube 46, which is optional, is employed to slightly increase the pressure in reboiler 42 to thereby raise the boiling point of benzene a degree or two. Likewise, a pressure generator 56 may be optionally employed to raise the pressure of the system. Other standard pressure increasing devices can be employed. Pressure can thus be increased in the system such that the boiling point of benzene increases up to about 200° C.

In FIG. 1, control mechanisms for heat shutoff 50 and pump shutoff 52 are depicted which serve to shut off heat and pump if the liquids level in the system rises to such levels. These control mechanisms are optional and may be included so that the catalyst bed does not come into contact with the bottoms of the reboiler. Line 60 connects pump shutoff 52 to the system above condenser 21.

Figure 2:
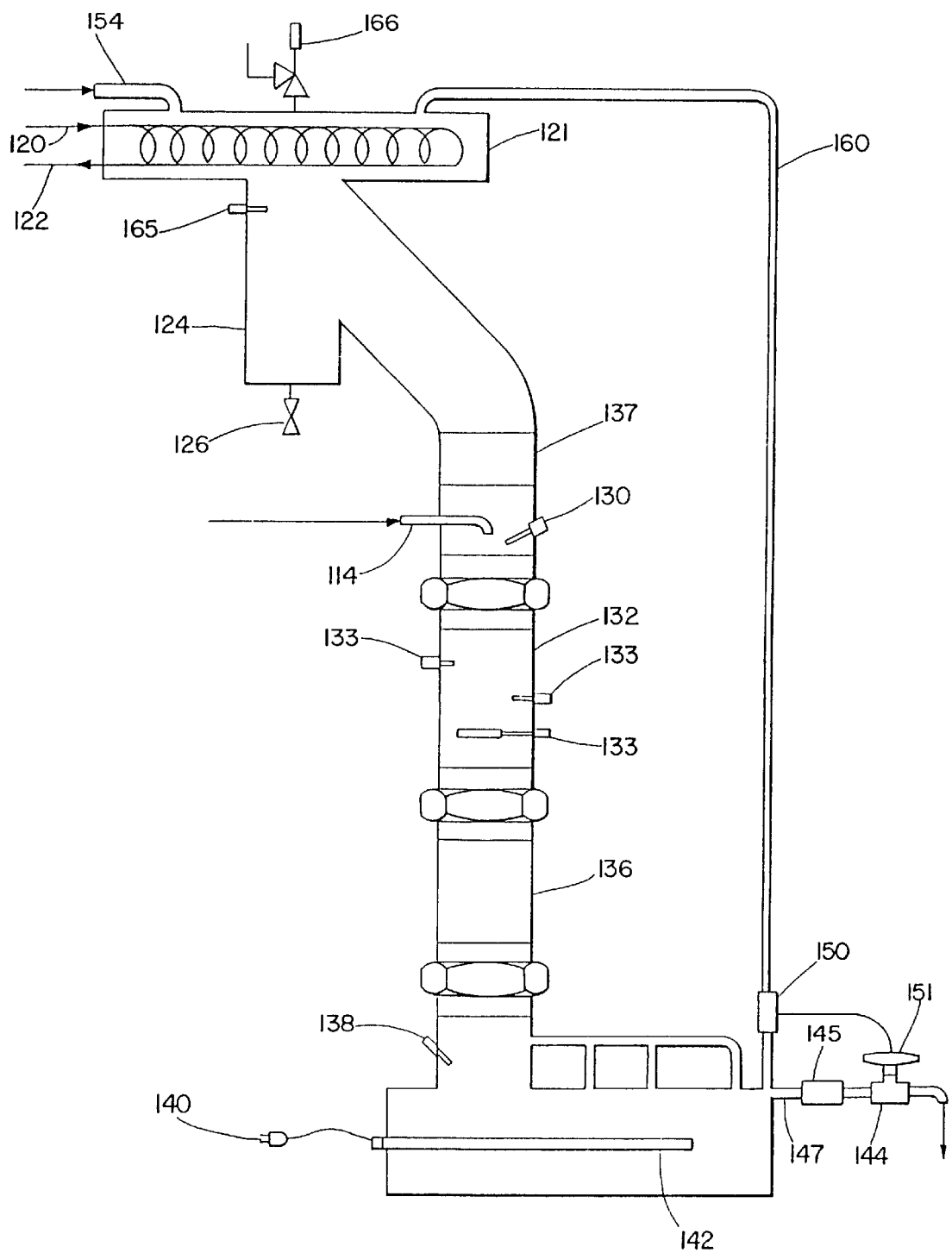
FIG. 2 shows a representation of a second continuous reactive distillation column employed in the practice of this invention.

In the practice of this invention in the alkylation of benzene, a wide variety of process conditions can be employed. In this regard, the temperature in the catalyst bed may vary depending on reactants, rate of introduction into the catalyst bed. size of the bed, and so forth. Generally, the bed is maintained at the reflux temperature of benzene depending on pressure. Typically, the temperature of the catalyst bed is above about 70° C., and most likely about 78° C. or more, in order to have reasonable reaction rates, and about 200° C. or less to avoid degradation of reactants and products and to avoid deactivation of the catalyst as by coke build-up. Preferably, the temperature is in the range from about 80° C. to about 140° C. The process may be operated at a variety of pressures during the contacting step, with pressures of about atmospheric most typically being employed. When the process is operated using a system as depicted in FIG. 1 and FIG. 2, the reboiler temperature is maintained such that benzene and olefin vaporize, the temperature varying depending on olefin, and generally being from about 80° C. to about 250° C. for olefins having 10 to 14 carbons. The composition of the reboiler will vary over time, but is generally set initially to have a benzene to olefin ratio of about 5:1, with this ratio being maintained during the practice of this invention. The rate of introduction of feed into the catalyst bed may vary, and is generally at a liquid hourly space velocity ("LHSV") of about 0.05 $hr^{-1}$ to about 10 $hr^{-1}$, more typically from about 0.05 $hr^{-1}$ to about 1 $hr^{-1}$. The mole ratio of benzene to olefin introduced into the catalyst bed is generally from about 1:1 to about 100:1. In commercial benzene alkylation operations, it is common to run at mole ratios of from about 2:1 to about 20:1, which can suitably be employed in the practice of this invention, and to charge said olefins as an olefin-paraffin mixture comprising 5% to 20% olefin content. Said olefin-paraffin (HC) mixtures are normally generated commercially through dehydrogenation of the corresponding paraffin starting material over a noble metal catalyst.

Another preferred embodiment of the continuous reactive distillation apparatus is depicted in FIG. 2. In FIG. 2, the feed mixture enters the reactor via feed inlet 114. The feed mixture falls through the column into catalyst bed 132, wherein alkylation to form LAB occurs. Thermowells 133 monitors the temperature of said catalyst bed 132. The catalyst bed 132 may be optionally heated externally and is contained within 1 ¼ inch stainless steel tubing. Goodloe packing is positioned at packing 136 and 137. LAB product, as well as unreacted benzene and olefin, fall through packing 136 into reboiler 142. In reboiler 142. electric heater 140 heats the contents of reboiler 142 such that heated vapors of benzene and olefin rise from the reboiler 142 to at least reach catalyst bed 132. As needed, the bottoms LAB product may be removed from reboiler 142 by opening bottoms valve 144 after passing through line 147 and filter 145. Residual water from the feed mixture, or which otherwise enters the system, may be condensed at condenser 121 which is cooled with coolant via outlet line 120 and inlet exit line 102. The condensed water falls to water trap 124, which can be drained as needed by opening drain valve 126. Temperature in the system is monitored via thermocouples 138. 130, and 165. The system includes pressure release valve 166. A nitrogen blanket over the system is maintained by introduction of nitrogen gas via inlet line 154. Level control activator 150 activates bottoms level control valve 151 to open when the liquids level in the reboiler rises to the level control activator 150. Line 160 connects level control activator 150 to the system above condenser 121. In this preferred embodiment, the catalyst distillation structure comprises extrudates, granules or tablets.

While the systems depicted in FIG. 1 and FIG. 2 show single catalyst bed systems. It may be appreciated that multi-catalyst bed reactors are within the scope of this invention, as well as multiple ports for inlet feeds, water traps, product removal lines, and so forth. Moreover, the process may be run in batch mode, or in other continuous processes using plugflow designs, trickle bed designs, and fluidized bed designs.

The following examples are illustrative of the present invention and are not intended to be construed as limiting the scope of the invention or the claims. Unless otherwise indicated, all percentages are by weight. In the examples, all reactants were commercial grades and used as received. The apparatus depicted in FIG. 1 was employed for most of the following examples. The equipment of FIG. 2 was used in Examples 11, 12, 17 and comparative Example 2.

It may be noted that Example 1 illustrates benzene alkylation with 1-decene using a solid acid, fluorided clay catalyst and the process design of FIG. 1 comprising a column of solid acid catalyst, a liquid reboiler fitted with product takeoff, water collection and takeoff, and a feed inlet above the catalyst bed. Typical data in Table 1 show greater than 95% 1-decene conversion per pass, 10–17% total decylbenzene product ($\Sigma Ph\text{-}C_{10}$) effluent concentrations, and 37–38% 2-phenyldecane (2-Ph-$C_{10}$) selectivities.

Examples 2–8 illustrate benzene alkylation runs using similar technology, but where the production of total decylbenzene product, $\Sigma Ph\text{-}C_{10}$ is shown as a function of changes in benzene/1-decene feed rates (LHSV varied from 0.4–1.0), feed composition (benzene/1-decene molar ratio varied from 20:1 to 5:1), selected olefin (benzene/1-octene=20:1), reactor tube diameter (varied from 1"–15⁄8") and catalyst life (200 hr).

Example 9 shows the use of a solid acid zeolite (β-zeolite) catalyst in the same equipment and where 2-Ph-$C_{10}$ selectivity is 50%.

Example 10 illustrates alkylation of benzene using another solid acid zeolite (dealuminized mordenite) in the same unit and using a benzene plus olefin/paraffin feed mix. Good catalyst life is realized with this mordenite using HC feed mix.

Examples 11 and 12 demonstrate benzene alkylation with 1-decene in a pressurized version of the unit, shown in FIG. 2, using either acidic fluorided clay or β-zeolite catalyst.

Examples 13–21 illustrate LAB production using the process and system of the present invention with the preferred flouride-treated mordenite catalyst. In particular, Example 14 illustrates LAB production from paraffin dehydrogenate using the fluoride-treated mordenite catalyst of example B, where good catalyst life (250+hrs) is achieved without catalyst regeneration, while maintaining a 2-phenyl LAB selectivity of >70% and high LAB productivity without significant loss of fluoride. Comparative example 1, on the other hand, using untreated mordenite, with no fluoride added, shows a rapid decline in LAB production. In addition, examples 15 and 16 illustrate LAB production using a 5:1 molar benzene/$C_{10}$-$C_{14}$ olefin feed mix and the fluoride-treated mordenite catalysts of Example B when operating at different LHSV's in the range of 0.2–0.4 $hr^{-1}$. Example 16 shows 2-phenyl LAB selectivity of >70% coupled with high LAB productivity over a time period greater than 400 hours. Example 15 shows that catalyst life may exceed 500 hours without catalyst regeneration. Example 17 illustrates LAB production with the fluoride-treated mordenite catalyst where the alkylation is conducted at higher temperatures and under pressure. Examples 18–20 illustrate the performance of three HF-treated mordenite catalysts with different fluoride loadings. Example 21 shows how virtually no alkylation activity is observed with a highly-fluorinated mordenite.

Comparative Example 2 shows the poor alkylation performance of the LAB production unit of FIG. 2 when the $C_{10}$–$C_{14}$ paraffin dehydrogenate is injected separately from the benzene, at a point midway up the catalyst bed. In this comparative example, lower alkylate concentrations were obtained and higher concentration of heavies were observed.

Examples A and B illustrate the preparation of fluoride-treated mordenite catalyst.

EXAMPLE 1

This example illustrates an improved, continuous benzene alkylation using a solid acid, fluorided clay catalyst and the process design of FIG. 1.

Benzene alkylation with 1-decene was conducted using the process unit design of FIG. 1, attached. The process unit comprises the following principal features: a column of solid acid catalyst, packing columns above and below the catalyst bed, a liquid reboiler fitted with a liquid bottoms product takeoff, a condenser fitted with water collection and takeoff, a feed inlet above the catalyst column and the necessary temperature and pressure controls.

In this example, alkylation was conducted by first charging 100 ml of benzene/1-decene (20:1 molar) mix to the reboiler and 250 cc of solid acid clay catalyst (0.5% HF on acidic montmorillonite clay granules dried in vacuum, 20/60 mesh) to the 1" diameter reaction zone. The solid acid catalyst was held in place using Goodloe packing. The reboiler mixture was then heated to reflux and a benzene/1-decene mixture (20:1 molar) was continuously introduced into the unit above the catalyst column at the rate of 20 cc/hr (LHSV=0.08).

Under steady state conditions, liquid product was continuously withdrawn from the reboiler and water taken off from the water trap. The crude liquid product was periodically analyzed by gas-liquid chromatography (hereinafter "GLC"). Results are summarized in Table 1.

TABLE 1

Example 1 Results (Benzene/1-Decene Feed)

| Time On-stream (hrs) | Sample | $\Sigma$Ph-$C_{10}$ Concentration (%) | 2-Ph-$C_{10}$ Selectivity (%) | $\Sigma C_{10}^-$ |
|---|---|---|---|---|
| | 0[a] | 10.4 | 38 | 0.4 |
| 2 | 1 | 12.4 | 38 | 0.3 |
| 4 | 2 | 14.0 | 37 | 0.4 |
| 6 | 3 | 17.2 | 38 | 0.3 |
| 8 | 4 | 15.3 | 38 | 0.3 |
| 14 | 5[b] | 11.9 | 38 | 0.1 |
| 21 | 6[b] | 12.8 | 38 | 0.1 |

[a]Benzene/1-decene (20:1) in reboiler brought to reflux
[b]Shut down overnight

EXAMPLES 2–8

These examples illustrate continuous benzene alkylation using the same solid acid clay catalyst of Example 1 and the process design of FIG. 1, but with a variety of process modification.

Following the procedures of Example 1 and using the equipment of FIG. 1, alkylation of benzene was conducted as described in Example 1 but with the following modifications:

Example 2: The benzene/1-decene feed rate was increased to 100 cc/hr (LHSV 0.4)—see Table 2.

Example 3: The reaction zone inner diameter was increased to 1 5/8"—see Table 3.

Example 4: The benzene/1-decene feed rate was further increased to LHSV 1.0—see Table 4.

Example 5: The benzene/1-decene feed molar ratio was lowered to 10:1—see Table 5.

Example 6: The benzene/1-decene feed molar ratio was further lowered to 5:1—see Table 6.

Example 7: 200 hr of solid acid clay catalyst life without significant loss of activity was demonstrated—see Table 7.

Example 8: Benzene alkylation with 1-octene was demonstrated—see Table 8.

TABLE 2

Example 2 Results (Benzene/1-Decene Feed)

| Time On-stream (hrs) | Sample | $\Sigma$Ph-$C_{10}$ Concentration (%) | 2-Ph-$C_{10}$ Selectivity (%) | $\Sigma C_{10}^-$ | Weight (g) |
|---|---|---|---|---|---|
| | 0[a] | 23.5 | 39 | 0.1 | |
| 2 | 1 | 9.6 | 38 | <0.1 | |
| 4 | 2 | 11.5 | 38 | <0.1 | |
| 6 | 3 | 11.3 | 38 | <0.1 | |
| 13 | 4[b] | 12.2 | 38 | <0.1 | |
| 20 | 5[b] | 12.7 | 37 | <0.1 | |
| 28 | 6[b] | 9.4 | 36 | <0.1 | |
| 36[f] | 7[b] | 9.9 | 36 | <0.1 | |
| | Effluent -1[c] | 92.3 | 36 | 0.1 | 203 |
| | Effluent -2[c] | | | | 212 |

[a]Reboiler liquid: product from run Example 1
[b]Shut down overnight
[c]Stripped product EXAMPLE 2 Remarks
250 cc of the catalyst from Example 1 was used: acidity= 0.45 meq/g; $H_2O$=0.73% LHSV=0.4
Characteristics of recovered catalyst: acidity=0.47 meq/g; $H_2O$=2.0%

TABLE 3

Example 3 Results (Benzene/1-Decene Feed)

| Time On-stream (hrs) | Sample | $\Sigma$Ph-$C_{10}$ Concentration (%) | 2-Ph-$C_{10}$ Selectivity (%) | $\Sigma C_{10}^-$ | Weight (g) |
|---|---|---|---|---|---|
| | 0[a] | 11.3 | 36 | <0.1 | |
| 2 | 1 | 13.7 | 37 | <0.1 | |
| 4 | 2 | 11.3 | 37 | <0.1 | |
| 6 | 3 | 10.8 | 37 | <0.1 | |
| 14 | 4[b] | 11.2 | 36 | <0.1 | |
| 21 | 5[b] | 8.4 | 35 | <0.1 | |
| 29 | 6[b] | 9.7 | 36 | <0.1 | |
| 37 | 7[b] | 9.1 | 35 | <0.1 | |
| | Effluent[c] | 94.6 | 35 | 0.1 | 216 |

[a]Reboiler liquid: product from Example 2
[b]Shut down overnight
[c]Stripped product EXAMPLE 3 Remarks
250 cc of the catalyst from Example 1 was set in a 1 5/8" diameter column LHSV=0.4

Characteristics of recovered catalyst: acidity=0.44 meq/g; $H_2O$=4.9%

TABLE 4

Example 4 Results (Benzene/1-Decene Feed)

| Time On-stream (hrs) | Sample | $\Sigma$Ph-$C_{10}$ Concentration (%) | 2-Ph-$C_{10}$ Selectivity (%) | $\Sigma C_{10}^-$ | Weight (g) |
|---|---|---|---|---|---|
| | 0[a] | 8.4 | 36 | <0.1 | |
| 2 | 1 | 24.5 | 37 | 3.8 | |
| 5 | 2 | 8.8 | 37 | 5.0 | |
| 6 | 3 | 2.4 | 38 | 2.4 | |
| 14[b] | 4 | 2.8 | 39 | 3.1 | |
| 22[b] | 5 | 2.5 | 40 | 3.0 | |
| 30[b] | 6 | 2.1 | 43 | 3.2 | |
| | Effluent[c] | 91.4 | 40 | | 99 |

[a]Reboiler liquid: product from run 7102-30
[b]Shut down overnight
[c]Stripped product

EXAMPLE 4 Remarks 200 cc of the catalyst from Example 1 was set in a 1 ⅝" diameter column LHSV=1.0

Characteristics of the recovered catalyst: acidity 0.46 meq/g; $H_2O$=3.8%

TABLE 5

Example 5 Results (Benzene/1-Decene Feed)

| Time On-stream (hrs) | Sample | $\Sigma$Ph-$C_{10}$ Concentration (%) | 2-Ph-$C_{10}$ Selectivity (%) | $\Sigma C_{10}^-$ | Weight (g) |
|---|---|---|---|---|---|
| | 0 | 0.2 | | 16.3 | |
| 2 | 1 | 5.5 | 35 | 13.1 | |
| 4 | 2 | 12.6 | 37 | 8.7 | |
| 6 | 3 | 15.1 | 37 | 4.7 | |
| 13[a] | 4 | 16.3 | 36 | 0.8 | |
| 21[a] | 5 | 16.9 | 35 | 0.2 | |
| 29[a] | 6 | 17.4 | 35 | 0.1 | |
| | Effluent[b] | 91.9 | 36 | 0.7 | 318 |

[a]Shut down overnight
[b]Stripped product

Example 5 Remarks 250 cc of the catalyst from Example 1 was set in a 1 ⅝" diameter column LHSV=0.4

TABLE 6

Example 6 Results (Benzene/1-Decene Feed)

| Time On-stream (hrs) | Sample | $\Sigma$Ph-$C_{10}$ Concentration (%) | 2-Ph-$C_{10}$ Selectivity (%) | $\Sigma C_{10}^-$ | Weight (g) |
|---|---|---|---|---|---|
| | 0 | 1.3 | | 21.9 | |
| 2 | 1 | 7.5 | 36 | 22.7 | |
| 4 | 2 | 18.8 | 36 | 13.5 | |
| 6 | 3 | 24.2 | 36 | 8.3 | |
| 28 | 4 | 31.6 | 35 | 0.6 | |
| 46 | 5 | 21.7 | 36 | 5.8 | |
| 70[a] | 6 | 17.4 | 38 | 6.0 | |
| | Effluent[b] | 89.3 | 35 | 0.7 | 504 |
| 79 | 7B | 20.8 | 39 | 7.8 | |
| 87 | 8 | 16.8 | 40 | 8.9 | |
| 110 | 9 | 16.1 | 39 | 7.8 | |
| 135 | 10 | 15.6 | 40 | 9.1 | |
| 159 | 11 | 15.2 | 39 | 8.5 | |
| | Effluent[b] | 86.3 | 40 | 0.5 | 284 |

[a]Shut down over weekend
[b]Stripped product

Example 6 Remarks 250 cc of the catalyst from Example 1 was set in a 1 ⅝" diameter column LHSV=0.4

TABLE 7

Example 7 Results (Benzene/1-Decene Feed)

| Time On-stream (hrs) | Sample | $\Sigma$Ph-$C_{10}$ Concentration (%) | 2-Ph-$C_{10}$ Selectivity (%) | $\Sigma C_{10}^-$ | Weight (g) |
|---|---|---|---|---|---|
| | 0 | 1.3 | | 4.8 | |
| 2 | 1 | 8.4 | 37 | 6.9 | |
| 4 | 2 | 11.6 | 38 | 5.4 | |
| 6 | 3 | 11.6 | 37 | 2.8 | |
| 23 | 4 | 8.7 | 36 | 0.1 | |
| 46 | 5 | 11.7 | 37 | <0.1 | |
| 61 | 6 | 16.2 | 37 | <0.1 | |
| 95 | 7 | 15.9 | 36 | <0.1 | |
| 109 | 8 | 14.7 | 36 | 0.1 | |
| 133 | 9 | 14.4 | 35 | 0.2 | |
| 157 | 10 | 17.6 | 35 | 0.2 | |
| 165 | 11 | 16.3 | 35 | 0.2 | |
| 177 | 12 | 16.2 | 36 | 0.5 | |
| 201 | 13 | 14.0 | 37 | 0.7 | |
| | Effluent[a] | 93.9 | 36 | 0.2 | 209 |

[a]Stripped product

Example 7 Remarks 250 cc of the catalyst from Example 1 was set in a 1 ⅝" diameter column LHSV=0.4

TABLE 8

Example 8 Results (Benzene/1-Octene Feed)

| Time On-stream (hrs) | Sample | $\Sigma$Ph-$C_8$ Concentration (%) | 2-Ph-$C_8$ Selectivity (%) | $\Sigma C_8^-$ |
|---|---|---|---|---|
| | 0 | 7.9 | 40 | 1.5 |
| 2 | 1 | 8.9 | 40 | 1.1 |
| 4 | 2 | 11.6 | 40 | 1.1 |
| 5 | 3 | 9.2 | 40 | 0.9 |
| 23 | 4 | 9.9 | 40 | 0.2 |
| 44 | 5 | 9.9 | 40 | 0.2 |
| 81 | 6 | 10.2 | 40 | 0.1 |

Example 8 Remarks

Catalyst from Example 7 was used Feed=100 cc/hour (LHSV=0.4)

EXAMPLE 9

This example illustrates continuous benzene alkylation using a solid acid zeolite catalyst and the process design of FIG. 1.

Following the procedures of Example 1 and using the equipment of FIG. 1, alkylation of benzene was conducted as described, but using 250 cc of solid acid zeolite catalyst (80% beta zeolite, 20% alumina binder, 1/16" diameter extrudates). A benzene/1-decene mixture (20:1 molar) was fed continuously at a rate of 100 cc/hr. Under steady state conditions, product effluent samples exhibited the following characteristics:

| | |
|---|---|
| $\Sigma$Ph-$C_{10}$ concentration: | 9.7% |
| 2-Ph-$C_{10}$ selectivity: | 50% |
| $\Sigma C_{10}^-$ concentration: | 0.1% |

EXAMPLE 10

This example illustrates continuous benzene alkylation with a $C_{10}$–$C_{14}$ olefin/paraffin mixture using a solid acid zeolite catalyst and the process design of FIG. 1.

Following the procedures of Example 1 and using the equipment of FIG. 1, alkylation of benzene with a $C_{10}$–$C_{14}$ olefin/paraffin mixture was conducted as described in Example 1, but using 250 cc of another solid acid zeolite catalyst (dealuminized mordenite, $SiO_2/Al_2O_3$ [molar ratio 20:1], 1/16" diameter extrudates calcined at 538° C. and dried at 150° C.). A mixture of benzene and a $C_{10}$–$C_{14}$ olefin/paraffin mix (containing 8.5% olefin) was fed continuously at 100 cc/hr (LHSV=0.4). The benzene/olefin molar ratio was 10:1. Under steady state conditions, the product effluent was sampled and analyzed by GLC over approximately 100 hours of operation. The results are summarized in Table 9.

TABLE 9

Example 10 Results (Benzene/$C_{10}$–$C_{14}$ Olefin/Paraffin Feed)

| Time On-stream (hrs) | Sample | Alkylate Concentration (%) | $C_6H_6$ Concentration (%) |
|---|---|---|---|
| | 0 | — | 8.9 |
| 2 | 1 | 2.60 | 16.7 |
| 4 | 2 | 4.43 | 20.6 |
| 6 | 3 | 5.68 | 23.2 |
| 8 | 4 | 6.26 | 24.4 |
| 14 | 5 | 6.95 | 26.2 |
| 23 | 6 | 6.45 | 27.7 |
| 28 | 7 | 6.33 | 27.4 |
| 31 | 8 | 6.42 | 25.7 |
| 53 | 9 | 6.56 | 27.6 |
| 62 | 10 | 6.21 | 27.2 |
| 74 | 11 | 6.18 | 25.8 |
| 97 | 12 | 5.57 | 27.6 |

EXAMPLE 11

This example illustrates continuous benzene alkylation using a solid acid fluorided clay catalyst and a pressure unit design of the type shown in FIG. 2.

Benzene alkylation with 1-decene was conducted using a process unit of the type shown in FIG. 2, constructed of 316 stainless steel. About 100 ml of benzene/1-decene (20:1) molar mix was charged to the reboiler and 250 cc of solid acid catalyst (0.5% HF on acidic montmorillonite clay granules, 20/60 mesh) was charged to the 1 1/4" id reaction zone. The reboiler liquid was then heated to reflux and a benzene/1-decene mixture (20:1 molar) continuously introduced into the unit above the catalyst column at a rate of 100 cc/hr. Under steady state conditions, reaction conditions were maintained as follows:

| | |
|---|---|
| Reboiler temperature: | 132° C. |
| Reaction zone temperature range: | 70–100° C. |
| Exit pressure: | 4.1 psi |

Liquid product was continuously withdrawn from the reboiler and water taken from the water trap. The crude liquid product was periodically analyzed by GLC. Typical results were as follows:

| | |
|---|---|
| $\Sigma$Ph-$C_{10}$ concentration: | 15.1% |
| 2-Ph-$C_{10}$ selectivity: | 37% |
| $\Sigma C_{10}^-$ concentration: | <0.1% |

EXAMPLE 12

This example illustrates continuous benzene alkylation using a solid acid zeolite catalyst and a pressure unit design of the type shown in FIG. 2.

Benzene alkylation with 1-decene was conducted using a process unit of the type shown in FIG. 2. Following the procedure of Example 11, 250 cc of solid acid zeolite catalyst (80% β-zeolite, $SiO_2/Al_2O_3$ [molar ratio 23.9:1], 20% alumina binder, 1/16" diameter extrudates) was charged to the 1 1/4" diameter reaction zone. The reboiler liquid was then heated to reflux and a benzene/1-decene mixture (20:1 molar) continuously introduced into the unit above the catalyst column at a rate of 100 cc/hr. Under steady state conditions, reaction conditions were maintained as follows:

| | |
|---|---|
| Reboiler temperature: | 171° C. |
| Reaction zone temperature range: | 100–192° C. |
| Exit pressure: | 1.7 psi |

Liquid product was continuously withdrawn from the reboiler and water taken from the water trap. The crude liquid product was periodically analyzed by GLC. Typical results were as follows:

| | |
|---|---|
| $\Sigma$Ph-$C_{10}$ concentration: | 8.4% |
| 2-Ph-$C_{10}$ selectivity: | 47% |
| $\Sigma C_{10}^-$ concentration: | 1.8% |

EXAMPLE A

This example illustrates the preparation of a hydrogen fluoride-modified mordenite.

To 30 g of acidified mordenite (LZM-8, $SiO_2/Al_2O_3$ ratio 17; $Na_2O$ wt % 0.02, surface area 517 $M^2/g$, powder, from Union Carbide Corp.) was added 600 ml of 0.4% hydrofluoric acid solution, at room temperature. After 5 hours the solid zeolite was removed by filtration, washed with distilled water, dried at 120° C. overnight, and calcined at 538° C.

EXAMPLE B

The example illustrates the preparation of a hydrogen fluoride-modified mordenite.

To 500 g of acidified, dealuminized, mordenite (CBV-20A from PQ Corp.; $SiO_2/Al_2O_3$ molar ratio 20; $Na_2O$, 0.02 wt %; surface area 550 $m^2/g$, 1/16" diameter extrudates, that had been calcined at 538° C., overnight) was added a solution of 33 ml of 48% HF solution in 1633 ml of distilled water, the mix was cooled in ice, stirred on a rotary evaporator overnight, then filtered to recover the extruded solids. The extrudates were further washed with distilled water, dried in vacuo at 100° C., and then calcined at 538° C., overnight.

Analyses of the treated mordenite showed:

| F: | 1.2% |
|---|---|
| Acidity: | 0.49 meq/g |

EXAMPLE 13

This example illustrates the preparation of linear alkyl benzenes using a hydrogen fluoride-modified mordenite catalyst.

To a 500 ml flask, fitted with condenser and Dean Stark Trap was added 100 ml of benzene (reagent grade) plus 10 g of hydrogen fluoride-modified mordenite zeolite, prepared by the method of Example A. The mix was refluxed for 15–20 minutes to remove small amounts of moisture, then a combination of benzene (50 ml) plus 1-dodecene (10 g) was injected into the flask and the solution allowed to reflux for 3 hours.

Upon cooling, the modified mordenite catalyst was removed by filtration, the filtrate liquid flashed to remove unreacted benzene, and the bottoms liquid analyzed by gas chromatography.

Typical analytical data are summarized in Table 10.

TABLE 10

Example 13 Results (Benezene/1-Dodecene Batch)

| DODECENE CONV. (%) | LAB ISOMER DISTRIBUTION (%) | | | | | HEAVIES (%) | LINEAR LAB (LLAB) (%) |
|---|---|---|---|---|---|---|---|
| | 2-Ph | 3-Ph | 4-Ph | 5-Ph | 6-Ph | | |
| 99.7 | 79.9 | 16.6 | 0.8 | 1.3 | 1.3 | 0.2 | 95.9 |

EXAMPLE 14

This example illustrates the preparation of linear alkyl-benzenes from paraffin dehydrogenate using a hydrogen fluoride-treated mordenite catalyst.

In the example, benzene was alkylated with a sample of $C_{10}$–$C_{14}$ paraffin dehydrogenate containing about 8.5% $C_{10}$–$C_{14}$ olefins. Alkylation was conducted in a process unit as shown in FIG. 1.

Alkylation was conducted by first charging 500 ml of a benzene/paraffin dehydrogenate mix (10:1 molar ratio, benzene/$C_{10}$–$C_{14}$ olefin) to the reboiler and 250 cc of the HF-treated mordenite of example B to the 1.1" i.d. reaction zone. The mordenite was held in place using Goodloe packing. The reboiler liquid was then heated to reflux and a benzene plus $C_{10}$–$C_{14}$ paraffin dehydrogenate mix (10:1 molar ratio, benzene/$C_{10}$–$C_{14}$ olefin) continuously introduced into the unit above the catalyst column at the rate of 100 cc/hr. (LHSV=0.4 $hr^{-1}$).

Under steady state, reflux, conditions liquid product was continuously withdrawn from the reboiler and water continuously taken off from the water trap. The crude liquid product was periodically analyzed by gas chromatography. The reboiler temperature was typically in the controlled range of 97–122° C. The column head temperature variability was 78–83° C. A summary of the analytical results may be found in Table 11.

After 253 hours on stream, the recovered HF-treated mordenite catalyst showed by analysis:

| F: | 1.1% |
|---|---|
| Acidity: | 0.29 meq/g |
| $H_2O$: | 0.3% |

TABLE 11

Example 14 Results (Benezene/$C_{10}$–$C_{14}$ Olefin/Paraffin Feed)

| Time on Stream (Hrs) | Sample | Alkylate Conc. (%) | 2-Phenyl Sel. (%) | $C_6H_6$ Conc. (%) |
|---|---|---|---|---|
| 0 | 0 | 1.4 | | 32.3 |
| 2 | 1 | 3.4 | | 19.7 |
| 4 | 2 | 5.8 | 74.9 | 16.6 |
| 6 | 3 | 6.6 | 75.8 | 25.2 |
| 32 | 4 | 7.9 | 80.7 | 27.0 |
| 56 | 5 | 7.8 | 82.7 | 27.0 |
| 69 | 6 | 7.3 | 81.4 | 27.4 |
| 94 | 7 | 6.5 | 82.0 | 27.8 |
| 118 | 8 | 6.0 | 78.4 | 27.7 |
| 142 | 9 | 5.9 | 81.3 | 26.9 |
| 166 | 10 | 5.4 | 81.5 | 27.3 |
| 207 | 11 | 5.3 | 81.3 | 26.1 |
| 229 | 12 | 5.1 | 81.1 | 27.4 |
| 253 | 13 | 4.9 | 81.4 | 28.1 |

COMPARATIVE EXAMPLE 1

This example illustrates the preparation of linear alkyl benzenes from paraffin dehydrogenate using an untreated mordenite catalyst.

Following the procedures of Example 14, the alkylation unit was charged with 250 cc of untreated, calcined, mordenite, (the starting mordenite of Example B), and the liquid feed comprised benzene plus $C_{10}$–$C_{14}$ paraffin dehydrogenate mix in a 10:1 molar ratio of benzene/$C_{10}$–$C_{14}$ olefin.

Typical results are summarized in Table 12.

The recovered mordenite showed by analysis:

| Acidity: | 0.29 meq/g |
|---|---|
| $H_2O$: | 2.1% |

TABLE 12

Example 14 Results (Benezene/$C_{10}$–$C_{14}$ Olefin/Paraffin Feed)

| Time on Stream (Hrs) | Sample | Alkylate Conc. (%) | 2-Phenyl Sel. (%) | $C_6H_6$ Conc. (%) |
|---|---|---|---|---|
| 0 | 0 | | | 11.2 |
| 2 | 1 | 6.50 | | 9.9 |
| 4 | 2 | 7.16 | 73.2 | 17.1 |
| 6 | 3 | 7.09 | 73.1 | 26.4 |
| 22 | 4 | 8.61 | 73.9 | 26.6 |
| 31 | 5 | 10.49 | 67.4 | 15.8 |
| 46 | 6 | 7.39 | 75.0 | 27.7 |
| 70 | 7 | 6.39 | 75.1 | 28.5 |

TABLE 12-continued

Example 14 Results (Benzene/$C_{10}$–$C_{14}$ Olefin/Paraffin Feed)

| Time on Stream (Hrs) | Sample | Alkylate Conc. (%) | 2-Phenyl Sel. (%) | $C_6H_6$ Conc. (%) |
|---|---|---|---|---|
| 93 | 8 | 6.08 | 73.6 | 23.0 |
| 144 | 9 | 5.21 | 73.6 | 15.8 |
| 157 | 10 | 4.40 | 73.9 | 26.2 |
| 180 | 11 | 3.06 | 69.6 | 27.1 |
| 204 | 12 | 1.32 | | 19.5 |
| 228 | 13 | 1.32 | | 33.3 |

EXAMPLE 15

This example also illustrates the preparation of linear alkyl benzene from paraffin dehydrogenate using a hydrogen fluoride-treated mordenite catalyst.

Following the procedures of Example 14, the alkylation unit was charged with 250 cc of the HF-treated mordenite of Example B, and the liquid feed comprised a benzene plus $C_{10}$–$C_{14}$ paraffin dehydrogenate mix in a 5:1 molar ratio of benzene/$C_{10}$–$C_{14}$ olefin, the reboiler temperature was typically in the range of 122–188° C., the column head temperature 78–83° C. Typical analytical results are summarized in Table 13.

After 503 hours on stream, the recovered HF-treated mordenite catalyst showed on analysis:

| F: | 1.0% |
|---|---|
| Acidity: | 0.35 meq/g |
| $H_2O$: | 0.1% |

TABLE 13

Example 15 Results (Benzene/$C_{10}$–$C_{14}$ Olefin/Paraffin Feed)

| Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|
| 0 | 0 | 1.0 | | 8.9 | 1.1 |
| 2 | 1 | 3.5 | 61.8 | 0.3 | 3.5 |
| 4 | 2 | 7.1 | 72.1 | 0 | 7.1 |
| 6 | 3 | 6.8 | 76.7 | 7.2 | 7.3 |
| 34 | 4 | 8.4 | 79.7 | 14.3 | 9.8 |
| 71 | 5 | 7.2 | 81.8 | 14.6 | 8.5 |
| 96 | 6 | 6.5 | 80.8 | 15.5 | 7.7 |
| 119 | 7 | 6.3 | 80.6 | 15.1 | 7.4 |
| 643 | 8 | 6.0 | 81.0 | 14.3 | 7.0 |
| 168 | 9 | 5.9 | 80.7 | 14.4 | 6.9 |
| 239 | 10 | 5.0 | 78.2 | 8.8 | 5.5 |
| 263 | 11 | 5.3 | 79.2 | 13.5 | 6.2 |
| 288 | 12 | 5.0 | 79.6 | 16.5 | 6.0 |
| 311 | 13 | 5.4 | 79.4 | 4.1 | 5.6 |
| 335 | 14 | 5.5 | 79.2 | 8.2 | 6.0 |
| 408 | 15 | 4.9 | 79.4 | 13.1 | 5.6 |
| 432 | 16 | 4.7 | 78.8 | 14.4 | 5.5 |
| 456 | 17 | 4.4 | 78.5 | 14.1 | 5.1 |
| 479 | 18[a] | 4.7 | 78.6 | 2.7[b] | 4.8 |
| 488 | 19[b] | 4.9 | 78.5 | 2.4[c] | 5.0 |
| 503 | 20[b] | 5.1 | 78.9 | 0.6[c] | 5.1 |

[a]Corrected for benzene in effluent sample.
[b]Applied pressure 8" $H_2O$
[c]Aplied pressure 12" $H_2O$

EXAMPLE 16

This example illustrates the preparation of linear alkyl benzene from paraffin dehydrogenate using a hydrogen fluoride-treated mordenite catalyst.

In the example, benzene was alkylated with a sample of $C_{10}$–$C_{14}$ paraffin dehydrogenate containing about 8.5% $C_{10}$–$C_{14}$ olefins. Alkylation was conducted in a process unit as shown in FIG. 1.

Alkylation was conducted by first charging 500 ml of a benzene/paraffin dehydrogenate mix (5:1 molar ratio, benzene/$C_{10}$–$C_{14}$ olefin) to the reboiler and 500 cc of a HF-treated mordenite to the 1.1" i.d. reaction zone. The mordenite was held in place using Goodloe packing. The reboiler liquid was then heated to reflux and a benzene plus $C_{10}$–$C_{14}$ paraffin dehydrogenate mix (5:1 molar ratio, benzene/$C_{10}$–$C_{14}$ olefin) continuously introduced into the unit above the catalyst column at the rate of 100 cc/hr (LHSV=0.2 hr$^{-1}$).

Under steady state, reflux, conditions liquid product was continuously withdrawn from the reboiler and water continuously taken off from the water trap. The crude liquid product was periodically analyzed by gas chromatography. The reboiler temperature was typically in the controlled range of 131–205° C. The column head temperature variability was 76–83° C. A summary of the analytical results may be found in Table 14.

TABLE 14

Example 16 Results (Benzene/$C_{10}$–$C_{14}$ Olefin/Paraffin Feed)

| Pressure (Inch $H_2O$) | Reboiler Temp. (° C.) | Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|---|---|
| 12 | 205 | 2 | 1 | 8.2 | 74.3 | 0.5 | 8.3 |
| | 193 | 4 | 2 | 9.2 | 75.0 | 0.4 | 9.2 |
| | 175 | 6 | 3 | 10.0 | 74.8 | 2.3 | 10.3 |
| | 204 | 21 | 4 | 12.7 | 78.7 | 0.3 | 12.7 |
| | 146 | 44 | 5 | 11.7 | 81.0 | 10.4 | 12.9 |
| | 136 | 68 | 6 | 11.5 | 81.8 | 10.0 | 12.7 |
| | | 2–3 days | C[b] | 11.6 | 81.4 | 9.4 | 12.7 |
| | 136 | 93 | 7 | 11.3 | 82.6 | 10.8 | 12.5 |
| | | 4–5 days | C-1[b] | 11.0 | 81.8 | 11.0 | 12.2 |
| | 142 | 165 | 8 | 10.4 | 83.0 | 11.4 | 11.5 |
| | 142 | 189 | 9 | 10.2 | 83.4 | 10.5 | 11.2 |
| | 146 | 213 | 10 | 9.7 | 80.2 | 11.2 | 10.7 |
| | 139 | 238 | 11 | 9.6 | 83.4 | 11.1 | 10.7 |
| | 143 | 261 | 12 | 9.9 | 81.9 | 11.0 | 11.0 |
| | 133 | 333 | 13 | 9.2 | 83.4 | 11.3 | 10.3 |
| | 138 | 356 | 14 | 8.9 | 83.5 | 11.1 | 9.9 |
| | 138 | 381 | 15 | 8.8 | 83.0 | 11.3 | 9.8 |
| | 131 | 405 | 16 | 8.7 | 82.8 | 11.2 | 9.7 |

[a]Corrected for benzene in effluent sample
[b]Composite product

EXAMPLE 17

This example illustrates the preparation of linear alkyl benzenes from paraffin dehydrogenate using a hydrogen fluoride-treated mordenite catalyst.

Following the procedures of Example 14, alkylation of benzene with $C_{10}$–$C_{14}$ paraffin dehydrogenate was conducted using the stainless-steel unit of FIG. 2, complete with an extended catalyst column, reboiler, condenser, and controls. About 750 cc of the HF-treated mordenite of Example B was charged to the column. The liquid feed comprised benzene plus $C_{10}$–$C_{14}$ paraffin dehydrogenate mix in a 10:1 molar ratio of benzene/$C_{10}$–$C_{14}$ olefin. The LHSV remained at about 0.13 hr$^{-1}$.

Alkylation was conducted over a range of column and reboiler temperatures and a range of exit pressures. Typical results are summarized in Table 15.

TABLE 15

Example 17 Results (Benezene/$C_{10}$—$C_{14}$ Olefin/Paraffin Feed)

| Column Temp (° C.) | Pressure DIFF (psi) | Pressure EXIT (psi) | Reboiler Temp. (° C.) | Time (Days) | Sample (#) | Alkylate Conc. (%) | 2-Phenyl Sel. (%) | $C_6H_6$ Conc. (%) | Corrected Alkylate Conc. (%)[a] |
|---|---|---|---|---|---|---|---|---|---|
| 79-47 | 0 | 4.9 | 100 | 1 | 15 | 2.5 | 61.3 | 14.3 | 2.9 |
| 77-53 | 0 | 4.1 | 100 | 2 | 16 | 2.6 | 64.4 | 17.3 | 3.1 |
|  |  |  |  |  | 16[b] | 2.8 | 67.0 | 16.8 | 3.2 |
| 105-58 | 0 | 6.2 | 130 | 3 | 17 | 5.1 | 72.3 | 16.3 | 6.0 |
| 105-64 | 0 | 7.9 | 137 | 4 | 18 | 6.0 | 67.5 | 14.0 | 6.8 |
| 99-78 | 0 | 5.9 | 130 | 5 | 19 | 5.7 | 70.1 | 16.0 | 6.7 |
| 115-90 | 0.2 | 5.7 | 130 | 6 | 20 | 5.5 | 70.1 | 16.1 | 6.4 |
| 136-92 | 0.1 | 4.6 | 130 | 7 | 21 | 6.4 | 69.3 | 16.0 | 7.4 |
| 130-92 | 0 | 6.0 | 130 | 8 | 22 | 5.9 | 67.0 | 15.7 | 6.9 |
| 136-96 | 0 | 5.5 | 150 | 8 | 23 | 6.8 | 69.1 | 15.6 | 7.8 |
| 137-96 | 0.1 | 5.1 | 150 | 8 | 24 | 6.9 | 67.2 | 14.7 | 7.9 |
| 136-96 | 0 | 5.1 | 150 | 9 | 25 | 6.2 | 67.3 | 15.9 | 7.2 |
| 136-96 | 0.1 | 3.9 | 150 | 10 | 26 | 6.2 | 68.6 | 15.0 | 7.1 |
| 156-102 | 0 | 5.4 | 170 | 11 | 27 | 7.4 | 71.8 | 17.6 | 8.6[c] |
| 145-109 | 0.1 | 4.6 | 170 | 12 | 28 | 8.8 | 69.0 | 9.6 | 9.7[c] |
| 160-101 | 0 | 6.8 | 170 | 13 | 29 | 8.2 | 62.9 | 13.0 | 9.3[c] |
| 155-103 | 0 | 6.0 | 170 | 13 | 30 | 8.0 | 62.0 | 13.1 | 9.0[c] |
| 162-101 | 0 | 7.9 | 170 | 14 | 31 | 7.8 | 57.9 | 10.7 | 8.6[c] |
| 160-115 | 0 | 5.2 | 190 | 14 | 32 | 6.7 | 65.5 | 12.3 | 7.9 |
| 161-107 | 0 | 6.3 | 190 | 15 | 33 | 7.4 | 56.1 | 15.3 | 8.5 |
| 168-106 | 0 | 5.1 | 190 | 15 | 34 | 7.3 | 55.3 | 13.5 | 8.3 |
| 157-115 | 0.1 | 4.6 | 190 | 16 | 35 | 6.2 | 61.1 | 27.2 | 7.9 |
| 151-105 | 0.2 | 4.8 | 210 | 17 | 36 | 9.5 | 58.9 | 3.4 | 9.5 |
| 156-105 | 0.2 | 5.4 | 210 | 18 | 37 | 6.5 | 58.6 | 3.1 | 6.9 |

[a]Corrected for $C_6H_6$ in Effluent Sample
[b]Composite Product
[c]Total Heavies Concentration (dialkylated aromatics plus tetralins) less than 0.5%

EXAMPLES 18–20

These examples illustrate the preparation of linear alkyl benzene using hydrogen fluoride-modified mordenite catalysts with different fluoride treatment levels.

Following the procedures of Example 13, the alkylation unit was charged with benzene (100 ml), a 10 g sample of hydrogen fluoride-modified mordenite prepared by the procedure of Example B, plus a mix of benzene (50 ml) and 1-decene (10 g). Three HF-treated mordenites were tested, having the composition:
Catalyst "C" 0.25% HF on mordenite (CBV-20A)
Catalyst "D" 0.50% HF on mordenite (CBV-20A)
Catalyst "E" 1.0% HF on mordenite (CBV-20A)

In each experiment, samples of the bottoms liquid fraction were withdrawn at regular periods and subject to gas chromatography analyses. The results are summarized in Table 16.

TABLE 16

Results of Examples 18–20 (Benzene/1-Dodecene Batch)

| CATALYST | TIME (min.) | % LLAB | % ISOS | % HVY | % 2 Ph | % 3 Ph | % 4 Ph | % 5 Ph | % 6 & 7 Ph |
|---|---|---|---|---|---|---|---|---|---|
| D (0.5% HF) | 10 | 11.75 | 0.14 | 0 | 73.36 | 21.87 | 2.89 | 0.94 | 1.02 |
|  | 20 | 12.43 | 0.21 | 0 | 72.97 | 21.96 | 3.14 | 1.13 | 0.81 |
|  | 30 | 12.88 | 0.21 | 0 | 72.67 | 22.13 | 3.03 | 1.16 | 1.01 |
|  | 40 | 12.27 | 0.22 | 0 | 73.02 | 21.92 | 2.85 | 1.06 | 1.14 |
|  | 50 | 12.15 | 0.98 | 0 | 72.46 | 21.67 | 3.21 | 1.17 | 1.49 |
|  | 50 | 12.24 | 1.01 | 0 | 72.53 | 21.63 | 3.23 | 1.12 | 1.44 |
|  | 60 | 12.28 | 0.21 | 0 | 72.96 | 22.07 | 2.93 | 1.14 | 0.91 |
|  | 60 | 11.98 | 0.21 | 0 | 72.97 | 22.21 | 2.93 | 1.17 | 0.83 |
| C (0.25% HF) | 10 | 12.2 | 0.18 | 0 | 72.54 | 22.46 | 3.21 | 0.98 | 0.82 |
|  | 20 | 12.7 | 0.39 | 0 | 71.51 | 22.61 | 2.91 | 1.02 | 2.13 |
|  | 30 | 12.52 | 0.21 | 0 | 71.96 | 22.68 | 2.96 | 1.04 | 1.36 |
|  | 40 | 12.75 | 0.21 | 0 | 71.84 | 22.67 | 3.22 | 1.02 | 1.25 |
|  | 50 | 12.98 | 0.21 | 0 | 71.57 | 22.81 | 3.16 | 1.08 | 1.39 |
|  | 60 | 12.54 | 0.21 | 0 | 71.45 | 22.81 | 3.19 | 1.12 | 1.44 |
|  | 60 | 12.33 | 0.21 | 0 | 71.61 | 22.87 | 2.92 | 1.05 | 1.31 |
| E (1.0% HF) | 10 | 10.56 | 0.05 | 0 | 75.19 | 19.41 | 2.18 | 3.22 |  |
|  | 20 | 12.95 | 0.15 | 0 | 74.36 | 19.23 | 3.01 | 3.4 |  |
|  | 30 | 13.44 | 0.18 | 0 | 74.11 | 19.42 | 3.2 | 3.27 |  |
|  | 40 | 13.16 | 0.15 | 0 | 74.16 | 19.38 | 3.12 | 3.34 |  |

TABLE 16-continued

Results of Examples 18–20 (Benzene/1-Dodecene Batch)

| CATALYST | TIME (min.) | % LLAB | % ISOS | % HVY | % 2 Ph | % 3 Ph | % 4 Ph | % 5 Ph | % 6 & 7 Ph |
|---|---|---|---|---|---|---|---|---|---|
|  | 50 | 13.1 | 0.15 | 0 | 74.43 | 19.16 | 3.21 | 3.28 |  |
|  | 60 | 12.83 | 0.15 | 0 | 74.28 | 19.49 | 2.88 | 3.35 |  |
|  | 60 | 12.87 | 0.16 | 0 | 73.82 | 19.97 | 2.8 | 3.2 |  |

EXAMPLE 21

This example illustrates the inactivity of a heavily loaded hydrogen-fluoride modified mordenite catalyst.

Following procedures similar to Example 14, the alkylation unit was charged with 100 cc of a hydrogen fluoride-treated mordenite (CBV-20A) prepared by the method of Example B but having a much higher loading of HF (fluoride content 4.8%). The acidity of said HF-treated mordenite was 0.15 meq/g.

No significant amount of alkylated product was detected by gas chromatography.

COMPARATIVE EXAMPLE 2

This example illustrates the poor performance of the second continuous reactive distillation reactor of FIG. 2 when the $C_{10}$–$C_{14}$ paraffin dehydrogenate feed component is injected into the catalyst bed, 132, at the midpoint, 133, rather than above the catalyst column at feed inlet point 114.

Following procedures similar to Example 17, the alkylation unit was charged with 750 cc of the hydrogen fluoride-treated mordenite prepared by the method of Example B. but the liquid feed components, benzene and $C_{10}$–$C_{14}$ paraffin dehydrogenate mix, were charged separately to the alkylation unit of FIG. 2. Benzene was charged above the catalyst column at feed inlet point 114 at a rate of 28 cc/hr. The $C_{10}$–$C_{14}$ paraffin dehydrogenate was charged separately at the midpoint, 133, of the catalyst bed at a rate of 72 cc/hr. Under steady state conditions, with a reboiler temperature of 170° C. and a reaction zone temperature range of 100–142° C., GLC analysis of typical product effluent liquid yielded the following results:

| | |
|---|---|
| Σ Alkylate Concentration: | 4.9% |
| 2-Phenyl Isomer Selectivity: | 72.2% |
| Σ $C_6H_6$ Concentration: | 7.5% |
| Σ Corrected Alkylate Concentration: | 5.3% |
| Σ Heavies Concentration: | 4.0% |

What is claimed is:

1. An apparatus for manufacturing alkylated aromatic compounds, comprising:

(A) a reactor containing a fixed bed of an alkylation catalyst;

(B) one or more inlets in the reactor for introducing all of an aromatic compound and an olefin or all of a mixture of aromatic compound and olefin above the catalyst bed;

(C) a reboiler for collecting, heating and refluxing unreacted aromatic compound descending from the reactor, the reboiler positioned below and in communication with the reactor, the reactor and reboiler being generally in vertical alignment; and (D) a means for withdrawing alkylated aromatic compound from the reboiler.

2. The system of claim 1, further comprising a means for mixing the aromatic compound and the olefin, the mixing means located above the catalyst bed.

3. The system of claim 2, wherein the mixing means is packing.

4. The system of claim 3, wherein the alkylation catalyst is selected from HF-treated montmorillonite clay, beta zeolite, mordenite or HF-treated mordenite.

5. The system of claim 1, further comprising a condenser for condensing unreacted aromatic compound and water positioned above and in communication with the reactor.

6. The system of claim 5, further comprising a means for collecting water positioned below and in communication with the condenser.

7. The system of claim 6, further comprising a means for increasing pressure in the system; the pressure means being connected to one or more locations selected from the condenser, water collection means, reactor, injector, reboiler or withdrawal means.

8. The system of claim 7, further comprising a means for controlling the liquid level in the system; the liquid level control means being connected to one or more locations selected from the withdrawal means, the reboiler, the reactor, the water collection means or the condenser.

* * * * *